United States Patent [19]

Thoma

[11] 4,051,841
[45] Oct. 4, 1977

[54] METHOD OF AND APPARATUS FOR AUTOMATICALLY CONTROLLING HEART-SYNCHRONIZED CIRCULATING PUMPS

[76] Inventor: Herwig Thoma, 40/5, Maroltingergasse, Vienna, Austria

[21] Appl. No.: 620,996

[22] Filed: Oct. 9, 1975

Related U.S. Application Data

[63] Continuation-in-part of Ser. No. 435,387, Jan. 21, 1974, abandoned.

[30] Foreign Application Priority Data

Jan. 31, 1973   Austria .................................. 851/73

[51] Int. Cl.² ............................................. A61B 5/02
[52] U.S. Cl. ............................................. 128/2.05 R
[58] Field of Search ............ 128/1 D, 2.05 R, 2.05 T, 128/2.06 A, 2.06 F, 2.06 R, 419 PG

[56] References Cited

U.S. PATENT DOCUMENTS

| | | | |
|---|---|---|---|
| 3,430,624 | 3/1969 | Flanagan et al. | 128/1 D |
| 3,618,615 | 11/1917 | Greatbatch | 128/419 PG |
| 3,720,199 | 3/1973 | Rishtow et al. | 128/1 D |
| 3,924,610 | 12/1975 | Thoma | 128/2.06 R |

OTHER PUBLICATIONS

Chesnut et al., "IEEE Transactions on Biomedical Electronics" vol. BME 12, Nos. 3 & 4, Jul–Oct. 1969, pp. 173–186.

*Primary Examiner*—William E. Kamm
*Attorney, Agent, or Firm*—John C. Smith, Jr.

[57] ABSTRACT

A method and apparatus for automatically controlling heart-synchronized circulating pumps; which method comprises obtaining the parameters needed for regulation by analyzing the blood pressure beat for beat and continuously regulating the pump by reference to the transient parameters thus obtained. An electrocardiogram (EKG) is taken and analyzed, the immediate past history of the heart beat is derived from the analysis and a calculation used to determine the control action exerted on a heart pump. The control action is exerted on the pump through the control action calculator. Thus the body of the patient is included in a closed regulating cycle.

14 Claims, 6 Drawing Figures

METHOD OF AND APPARATUS FOR AUTOMATICALLY CONTROLLING HEART-SYNCHRONIZED CIRCULATING PUMPS

This is a continuation-in-part of copending application Ser. No. 435,387 filed Jan. 21, 1974, now abandoned.

BACKGROUND OF THE INVENTION

This invention relates to a method of and an apparatus for automatically controlling heat-synchronized circulating pumps, which method consists in obtaining the parameters needed for regulation by analyzing the blood pressure and continuously optimizing the timing of the pumping cycle by reference to the data obtained from the pressure analyzer. The system comprises a pumping pulse computer for initial adjustment and a monitoring system for monitoring the functioning of the electrodes on the patient as well as the functioning of the pump.

The clinical employment of heart-synchronized circulating pumps for long periods has demonstrated that the development of an automatic control system is necessary. Only a few research teams have really concerned themselves with the problem (Kane G.R. et al: — Automatic Control of Intraortic Balloon Pumping. Trans. Amer. Soc. Artif. Int. Organs, 17, 1971). The advantage of such a control is that the apparatus requires no continuous operating attention. Where it is remembered that mechanical assistance of circulation is continued for up to several weeks, it will be apparent that for organizational and staff reasons uninterrupted supervision, operation and control of the apparatus is quite impossible. This at once gives rise to a problem which the present method and apparatus is designed to solve. Control is effected under the supervision of a monitoring system which prevents malfunctioning of the pump, particularly of the controller. Control by reference to a computer is clinically not acceptable primarily because the computer is more complicated to operate than a conventional machine without regulating control. Control requires the availability of data which characterize the effect of control. One major drawback of existing systems is that control requires the provision of a number of data which it is impossible clinically to provide. Such data are the work done by the heart, the blood flow through the atrio-ventricular valves and atrial pressures, which would be needed as input parameters.

DESCRIPTIONS OF THE PRIOR ART

Federico, U.S. Pat. No. 3,698,381 relates to a system for the control and recording of the pumping pressure of an intra-aortal ballon pump. The system contains a safety chamber known per se consisting of the primary volume which is occupied cyclically by compressed air and the secondary volume separated by a moveable diaphragm, which is in direct connection with the intraaortal balloon. The control and regulation of this secondary pressure is the task of the Federico device. The gas pressure is measured by a compression measuring apparatus, various positive and negative pressure levels are defined, the exceeding or undercutting of which permits a slow and in some cases also a quick emptying or filling of the secondary volume with helium gas. As a result of that and according to that disclosure, the operating pressure necessary for the intraaortal balloon is regulated continuously.

Rishton U.S. Pat. No. 3,720,199 describes the intraaortal pulsation of the ballon which contains a safety chamber, which permits in the secondary space to shift a constant volume. The balloon located in the patient is inflated with this shifted volume. Since however the balloon located in the patient must have a variable volume depending on the size of the patient, a return signal is necessary in the case of the Rishton arrangement, which signals to the device the volume of the balloon which just happened to have been used. This is accomplished by means of a safety connector, which corresponds in principal to an electric resistance in the connector comparable to the volume. Then the secondary part of the installation is filled with variable gas pressure depending on the size of the resistance. This apparatus too contains a control block not described in more detail, called "Delay and Exhaust Time Generator".

Chesnut, U.S. Pat. No. 3,426,743 relates to a system, which before insertion of the intraaortal balloon was also used clinically, is described in detail the extracorporeal counter pulsation. A hydraulically operated piston shifts blood cyclically, which is in direct connection with the circulation of the patient. The shifting takes place in such a way that during the active phase of the heart, blood is taken from the body and this blood is then pumped again into the patient during the recovery time of the heart. The speed of the pumping piston can be adjusted. The temporal adjustment of the pump takes place by hand.

Pantle, U.S. Pat. No. 3,171,892 relates to a method for recording the fetal heart action. It has been known that the fetal EKG is very greatly disturbed by the mother's EKG. Since the rows of pulses of the heart actions of mother and child have a variable frequency, it is possible to eliminate the EKG of the mother by electronic blackout. At the same time the method known per se of defining the so-called "gate impulse" is used. Such blackouts are absolutely customary in the area of news communications. The value of this invention which without doubt exists, lies in the special application on a special biological problem.

Horth, U.S. Pat. No. 3,524,442 relates to an arrhythmia detector which records the QRS complex. The temporal intervals of the Q, R and S blips (serrations) are measured and stored and compared with the succeeding values. Deviations in the case of this comparison are signaled as not normal. In this manner extrasystols can be determined by machine and signaled. In the case of the instant invention, in the "arrhythmia counter" unit essentially only deviations of the duration of period are utilized whereas, in contrast in Horth, the entire QRS complex was analyzed with a very expensive apparatus, which in further differentiation of the present invention is executed in digital technique and furthermore a differentiation from the T-wave is carried out.

The article by Chesnut entitled: "Assisted Circulation Controlled by Electronic Computation" relates to a method of the extracorporeal counter pulsation, the contruction of a control device for it, as well as experimental and clinical use of this system. It is identical with what has already been described in the above-referenced Chesnut patent. A part from the experimental and clincal use, nothing else has been described in that article, except for the hydraulic control already shown in the Chesnut patents of an external pumping system in accordance with the principle of counter pulsation inclusive of the electronic construction units for the control necessary therefor. As the title of the article states, the author was dealing with a special control which is carried out on the basis of electronic calculating processes. In contrast, the present invention does not deal with automatic regulation including the circulation of the patient. In the case of the present invention, the circulation of the patient lies directly in the chain of regulation. The regulating mechanisms described in the Chesnut article all refer to regulating mechanisms within the electronic-hydraulic system, especially as far as the speed of the piston movement is concerned. This piston movement which adequately with regard to it leads to a shifting of the blood, is the big problem in the case of the extracorporeal counter pulsation, since in the case of too great a speed of the blood, the traumatization of the blood becomes too great.

SUMMARY OF THE PRESENT INVENTION AND OBJECTS THEREFOR

It is the object of the invention to overcome the above drawbacks of the prior art and to provide a method of and an apparatus for automatically controlling heart-synchronized circulating pumps which forms a closed feedback loop or regulating cycle which includes the body of the patient, the method comprises obtaining the parameters needed for regulation by analyzing the blood pressure beat for beat and continuously regulating the pump by reference to the transient parameters thus obtained. The method according to the present invention requires the provision of only one input parameter namely the arterial blood pressure curve and, for effecting control, not even the absolute values of this pressure need to be known.

BRIEF DESCRIPTION OF THE DRAWINGS

The embodiments of the invention will now be described by way of example and with reference to the accompanying drawing, in which.

DESCRIPTION OF THE PREFERRED EMBODIMENTS

Figure 1:
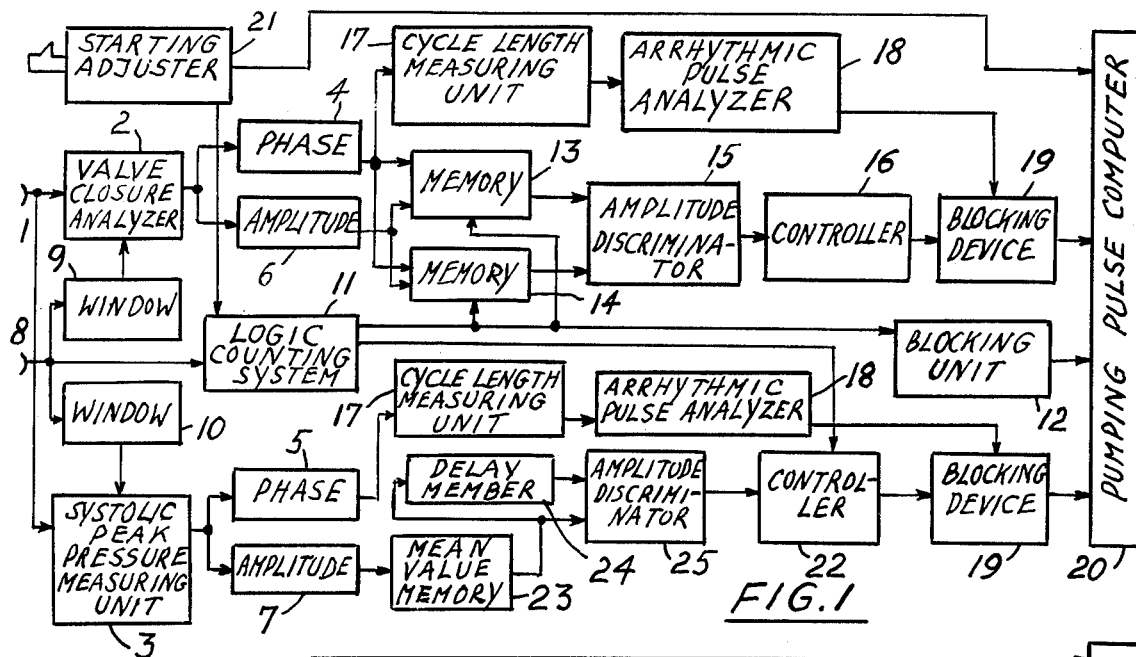
FIG. 1 is a block diagram of an embodiment of apparatus according to the invention.

FIG. 1 shows an arrangement which is suitable for all tandem pumping sets and for every method of counter-pulsation. From the pressure time curve, input 1, phases 4 and 5 and amplitudes 6 and 7 of the parameters "valve closure" and "systolic blood pressure" needed for control are determined by a valve closure analyzer 2 and a systolic peak pressure measuring unit 3. These events are related to the beginning of the cardiac cycle. Consequently, windows 9 and 10 are defined from the beginning of the cardiac cycle 7 input 8 by two monostable multivibrators and the pulse frequency described in detail hereinafter. The desired event can occur only within the phase range defined by the window. The trigger pulse derived from the heart beat at input 8 also drives a logic counting system 11 which at the beginning of control after a few pumping cycles interrupts the pumping action by means of a blocking unit 12 for one or more measuring cycles. Hence phase and amplitude of the valve closing pressure — controlled by the logic counting system 11 — can be stored, first with and then in the absence of pulsation. According to the invention these 2 × 2 measured values i.e. phase and amplitude of the valve closing pressure with and without pulsation, in two memories 13 and 14 are compared in an amplitude discriminator 15. Pump activation is curtailed by a controller 16 when the pressure amplitude at the time of valve closure, in the absence of pulsation, is greater than or equal to the pressure amplitude in the presence of pulsation. However, if the pressure during pulsation in the the said phase rises then the controller 16 will prolong the activation of the pump. The rhythm of the blood pressure time curve is monitored by a cycle length measuring unit 17 and an arrhythmic pulse analyzer 18 and the functioning of the controller can be stopped by blocking device 19. FIG. 1 also shows a pumping pulse computer 20 which usually obtains its information in the form of positive or negative pulses from the controllers 16 and 22. If the controllers are blocked the pumping pulse computer 20 computes the pumping pulse from the pulse frequency. When control begins, an uncritical pumping pulse is defined by a starting adjuster 21.

The end of the pumping pulse is controlled in continuous pulsation. A controller 22 starts by lengthening the pumping pulse under the control of the logic counting system 11. This lengthening depends upon the tendency of the values obtained by the systolic peak pressure measuring unit 3. According to the invention this tendency is ascertained by a comparison of the averaged amplitudes in a mean value memory 23 with past values which have been delayed by a delay member 24. If the tendency ascertained by an amplitude discriminator 25 is constant or falling, then the end of the pumping pulse is further delayed. If after optimum relief of the systolic peak has been achieved the tendency rises as the pumping pulse end continues to be delayed, then the end of the pumping pulse is now advanced. The phase 5 of the systolic peak value 3 is controlled as above by a cycle length measuring unit 17 and an arrhythmic pulse analyzer 18. This control can also be blocked 19. As described, according to the invention, the beginning of the pumping pulse is so controlled by reference to an analysis of the blood pressure time curve that the pumping pulse becomes effective directly after valve closure, the end of the pumping pulse being controlled so that the systolic peak pressure is a minimum.

DESCRIPTION OF THE BLOCK DIAGRAM IN FIG. 2

Figure 2:
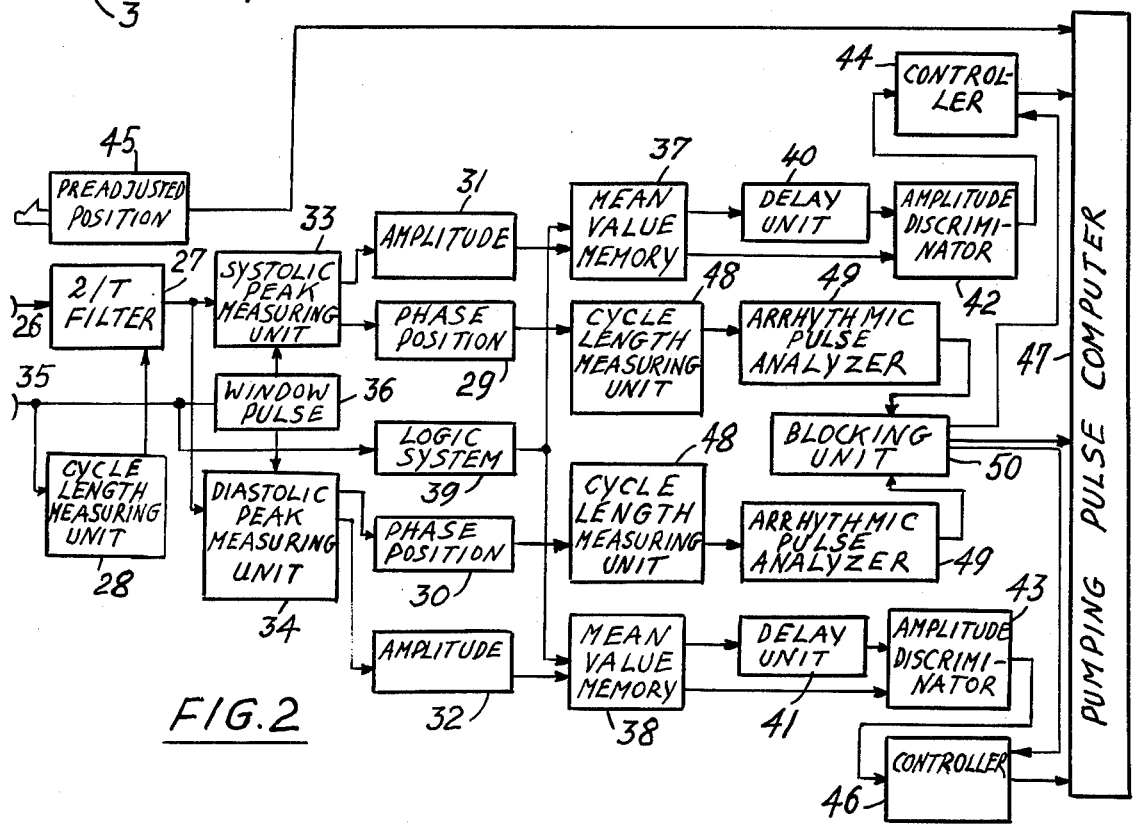
FIG. 2 is a block diagram of another embodiment.

It is not always possible to determine valve closure directly, for instance by frequency selection or differentiation of the pressure time curve. In clinical practice the available pressure curves are frequently damped. In such a case the invention proposes to employ what is termed the "2/T selection method." Tandem and counter-pulsation pumps generate a pressure curve with two peaks. The fundamental wave of this function does not have the frequency of the cycle length but twice the frequency (2/T). FIG. 2 shows an arrangement based on this principle: The course of the pressure time curve — input 26 — is filtered in a 2/T filter 27 of which the mean frequency is controlled by a cycle length measuring unit 28. With reference to the heart rate this signal has two maxima and their phase positions 29, 30 and amplitudes 31, 32 are measured by two peak measuring units 33 and 34. The functions of the systolic peak measuring unit 33 and of the diastolic peak measuring unit 34 are controlled by window pulses 35 controlled by ECG (input 35) (cf. FIG. 1). Control is effected either by determining the rising or falling tendency of the systolic and diastolic peaks. In FIG. 2 the reference numerals 37 and 38 denote mean value memories which are controlled by logic system 39. The reference numerals 40 and 41 denote delay units and the reference numerals 42 and 43 amplitude discriminators for determining the tendency of the systolic and diastolic pressure peaks. Analogously to the functioning of the system in FIG. 1 a controller 44 delays the end of the pumping pulse from a preadjusted position 45 when the tendency is constant or falling. A rising tendency causes the end of the pumping pulse to be advanced. Similarly the beginning of the pumping pulse is delayed by a controller 46 starting from a preadjusted position until the diastolic pressure peak is a maximum. When the starting adjustment 45 has been made a pumping pulse computer 47 obtains its information from the two controllers 44 and 46. The rhythm of the phase positions 29 and 30 of the systolic and diastolic peaks is checked by cycle length measuring units 48 and arrhythmic pulse analyzers 49 which cause the controllers to be automatically inactivated by a blocking unit 50 when the pulse trains are arrhythmic. This latter method gives optimum control for high heart rates, but at low rates control is imprecise because the instant of valve closure cannot be accurately determined. The special advantage of the method is the extreme insensitivity to irregularities in the blood pressure curve, particularly with regard to damping.

DESCRIPTION OF THE BLOCK DIAGRAM IN FIG. 3

Figure 3:
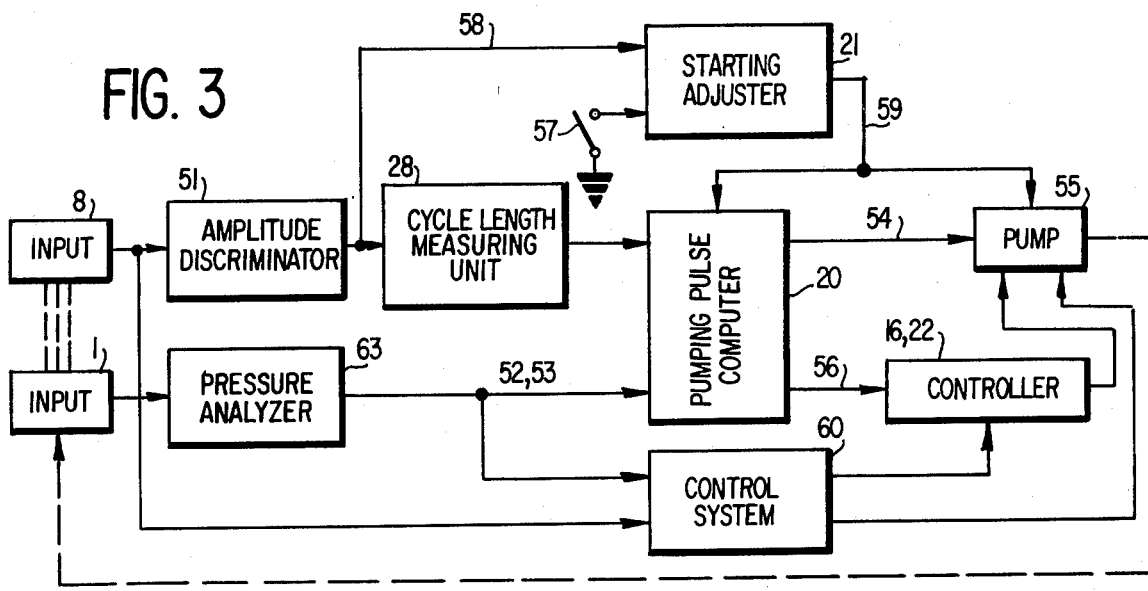
FIG. 3 is a block diagram of a preferred apparatus for automatically controlling a heart-synchronized circulating pump, and FIG. 4a and the combination of FIGS. 4b and 4c are block diagrams of subsystems incorporated in the block diagram of FIG. 3, which are applicable to the systems illustrated in FIGS. 1 and 2.
Figure 4A:
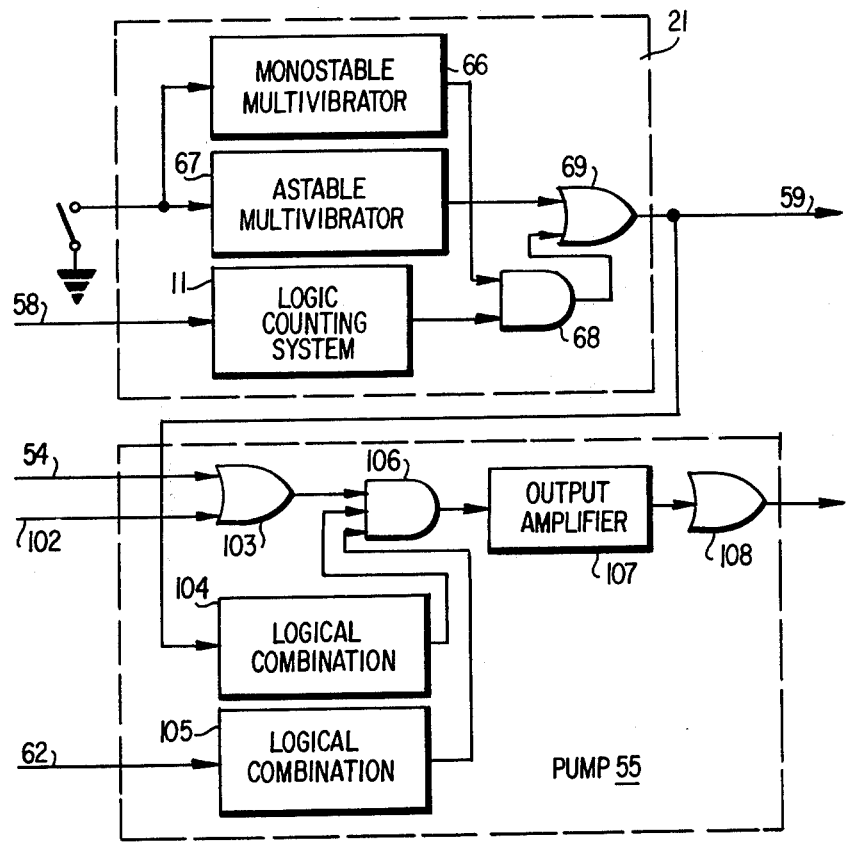
Figure 4B:
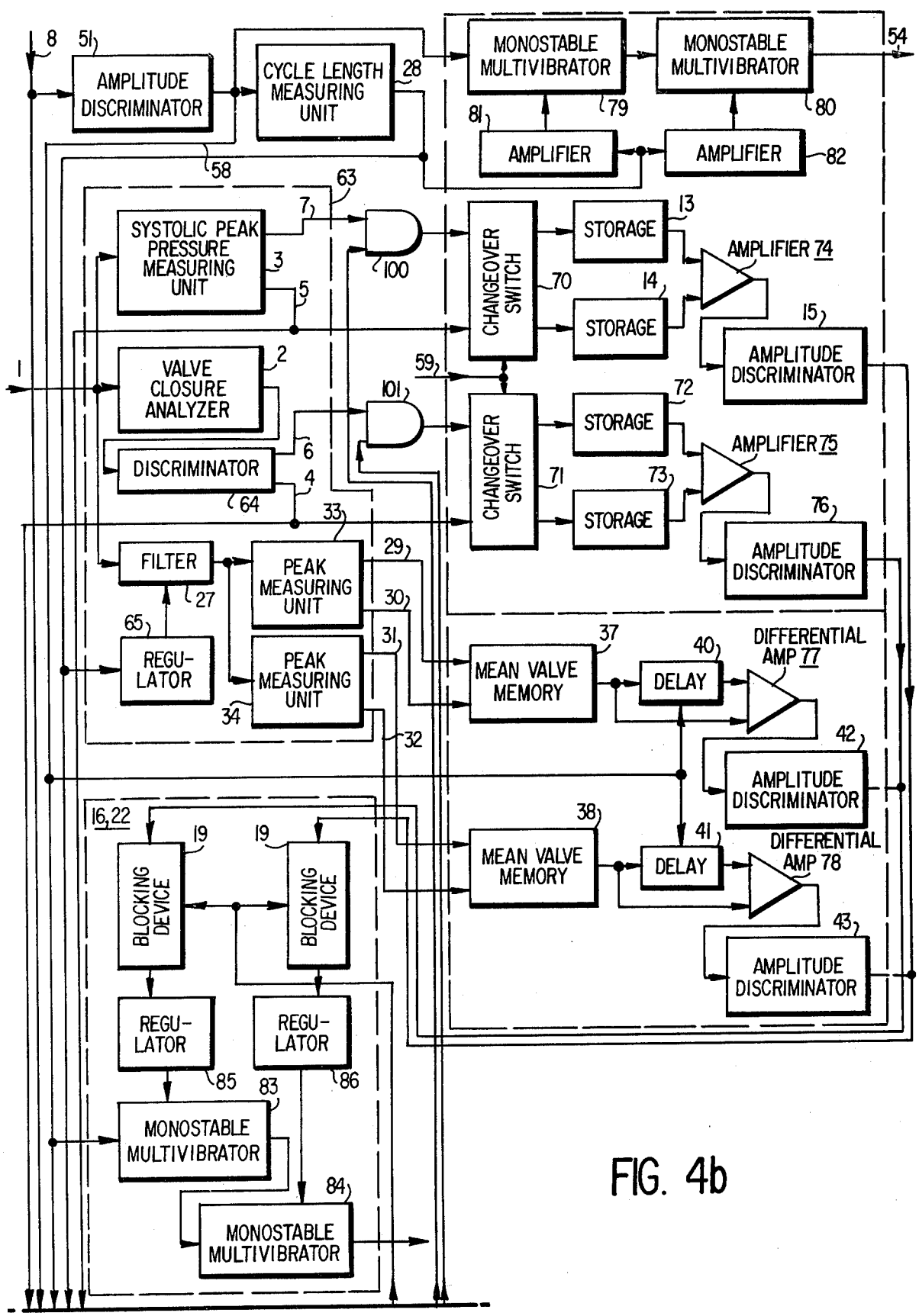
Figure 4C:
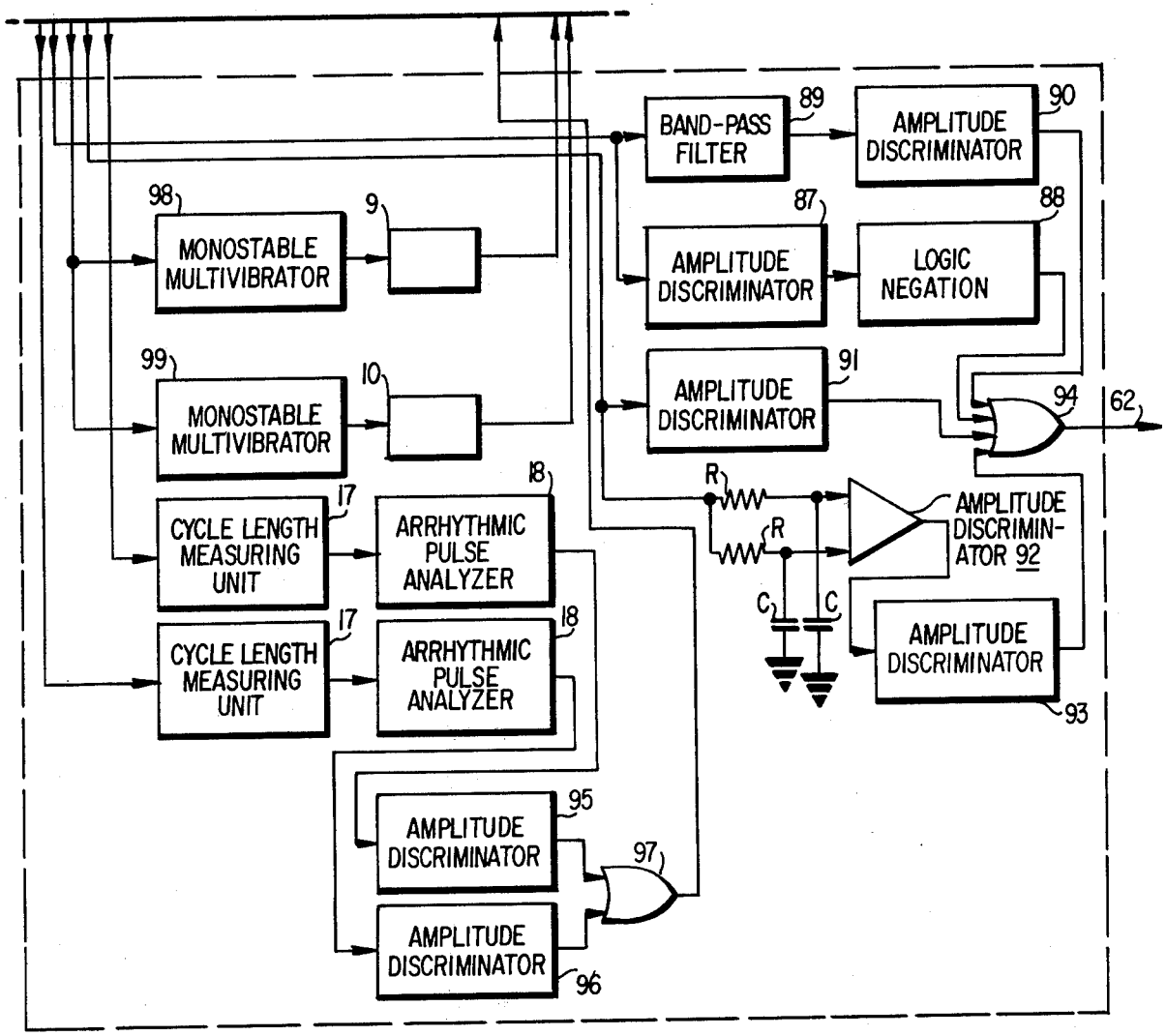

The simplified block diagram of FIG. 3 shows the essential construction groups of a further embodiment of the invention arranged slightly differently from FIG. 1. As illustrated, the beginning of the heart action of heart 8 is determined by way of amplitude discriminator 51. The heart cycle is measured pulse by pulse in period duration meter 28. Calculator 20 first of all calculates a non-critical pulse pump sequence. The course of the pressure in the circulation 1 is measured and is analyzed in the pressure analyzer 63 in order to determine characteristic values of the blood pressure. These characteristic values of the blood pressure, such as, for example, systolic peak pressure, amplitude and phase of the valve closure and the diastolic pressure dip are supplied to calculator 20 via the lines 52, 53 where they are analyzed and stored. The non-critical pumping impulses are fed to a pump 55 by way of a control line 54. The non-critical and thus ineffective pumping impulses are enlarged successively by the regulators 16, 22 until the optimum from the technical point of view of regulation has been reached. The regulator processes the characteristic values of the blood pressure carried by the calculator 20 by way of the line 56. From the point of view of regulating technique, always the characteristic values of the blood pressure in the case of a switched-on-pump are compared with the (a) standard and (b) theoretical values of blood pressure without the pump. This comparison becomes possible by way of the measuring cycle transmitter 21, which after switching on by way of the switch 57 will interrupt the pump by way of the line 59, controlled by the heart pulses by way of the line 58. The control system 60 checks the electrocardiogram and the characteristic values of the blood pressure and in the case of an occurrence of artefacts it will at first block the regulator by way of the line 61 and if necessary also the pump by way of the line 62. The construction groups according to FIG. 3 are shown in detail in, i.e. phase and amplitude of the valve closing pressure with and without pulsation, The pressure analyzer 63 contains a detector 3 (also see FIG. 1) for recording of the phase 5 and amplitude 7 of the systolic and/or diastolic peak of the blood pressure as well as a high pass filter or differentiator 2 with series connected amplitude 6 of the valve closure. The differentiator 2 triggers a discriminator 64 which analyzes phase 4 and amplitude 6 of the pressure of the valve closure. For realization of the method described according to FIG. 2, the pressure analyzer 63 furthermore contains an adjustable bandpass filter 27, preferably a Wien filter, a regulator 65 controlled by the pertinent duration meter 28 for adjusting of the selective frequency to precisely double the value of the heart frequency and always two detectors 33, 34 series connected to the Wien filter for determining the phase 29, 30 and amplitude 31, 32 of the systolic and diastolic peak of the blood pressure.

The measuring cycle transmitter 21 is enabled by way of the on/off switch 57. It contains a monostable multivibrator 66 preferably with a scanning time of about 2 minutes, an astable multivibrator 67 with about the same duration of the cycle, an electronic counter 11 controlled by the electrocardiogram or blood pressure, an AND gate 68 for connecting the outlets of the monostable multivibrator 66 and of the counter 11, as well as an OR gate 69 for connecting the outlets of the astable multivibrator 67 and of the AND gate 68. As a result of that the blocking 12 of the pump function becomes possible by way of line 59. The changeover switches 70, 71 located in the calculator 20 are also controlled via this line 59. The calculator 20 processes the amplitude and phase of the valve closure and/or of the systolic pressure peak. These characteristic values of the blood pressure will reach either the storages 13, 72 for storing of characteristic values while the pump is switched on, or the storages 14, 73 for storing of the (a) standard and (b) theoretical values of blood pressure while the pump is switched off by way of the changeover switches 70, 71 controlled electronically by way of the measuring cycle transmitter 21. Always two assigned storages will operate always one differential amplifier 74, 75 with series connected amplitude discriminator 15, 76. The amplitude discriminator, depending on the difference of the amplitudes delivers a positive or negative signal on the one hand with the pump and on the other hand without the pump. A positive signal of the amplitude discriminator leads to a successive broadening of the impulse. A negative signal leads to a successive reduction of the pumping impulse. This reduction or enlargement takes place by way of the lines 56 in the regulator 16, 22. In order to carry out the method according to FIG. 2, the calculator 20 furthermore always contains a storage 37, 38 for storing the systolic or diastolic peak of the blood pressure. Preferably these values are averaged. The differential amplifiers 77, 78 now always compare present with past values. The past values are stored by means of intermediate storage in the delaying members 40, 41 controlled by the amplitude discriminator 51. An amplitude discriminator 42 or 43 series connected with the pertinent differential amplifiers serves for the differentiation of the amplitude differences used for regulation.

Uncritical pumping pulses are produced by the calculator 20 as follows: The pulses of the amplitude discriminator 51 operate a monostable multivibrator 79, the latter operates a further monostable multivibrator 80 connected in series. The scanning time of these multivibrators is varied by amplifiers 81, 82 for the characteristic curves. The amplifiers for the characteristic curves are controlled by a meter for the duration of the periods 28. The control is accomplished in such a way, that the uncritical impulses viewed temporally will always lie about in the middle of the diastole. In the case of a reduction of the heart frequency, the scanning time of the two multivibrators is thus successively increased. A line 54 leads from the outlet of the multivibrator 80 to the pump 55.

The regulator 16, 22 too is operated by the pulses of the amplitude discriminator 51 and contains two monostable multivibrators 83, 84 connected in series. The scanning time of the multivibrators is influenced by the two regulators 85, 86. This influencing takes place as has already been described, by way of lines 56 in such a way, that in case of positive signals, the pumping pulse is broadened, in case of negative signals the pumping pulse is made narrower. Electronic switches 19 for blocking the regulating process are located within the line 56.

The control system 60 analyzes the occurrences from the electrocardiogram, low voltage, hum (buzz), tachycardia and arrhythmia as follows: The amplitude of the EKG is discriminated by way of the amplitude discriminator 87. The information by way of "low voltage" develops after a logical negation 88. Furthermore, the EKG reaches the subsequent amplitude discriminator 90 for the detection of external voltages in the EKG, by way of a band-pass filter 89 adapted to the grid frequency. A tachycardia can be registered as a result of discrimination 91 of the amplitude of the period duration meter 28. Arrhythmia of the sequence of the heart beat can be recognized by amplitude fluctuations at the outlet of the period duration meter 28. Preferably these fluctuations can be registered by way of a differential amplifier 92, at the inlets of which variable RC sections are attached. Similarly as in the case of a differentiator, the starting voltage of the differential amplifier is large, viewed absolutely, whenever a great difference of the amplitude of the period duration exists. The amplitude discriminator 93 differentiates a critical measure of arrhythmia from those period duration fluctuations which occur customarily within the scope of the biorhythm. The outlets of the pertinent amplitude discriminators 90, 87, 91, 93 are conducted or an OR-gate 94 so that in the case of a positive signal, the pump can be blocked by way of the line 62.

The control system 60 furthermore controls the regularity of the characteristic values of the blood pressure supplied by the pressure analyzer. This regularity is carried out analogously to the method described in the last paragraph by way of period duration meters 17. Every outlet of the period duration meters 17 is always connected with a differential amplifier 18 provided with variable RC sections at the inlet. The measure of the arrhythmia is determined in the series connected amplitude discriminators 95, 96. An OR gate 97 signals each occurrence at its outlet. Such an occurrence blocks the function of the regulator 16, 22 by way of the line 61.

Every characteristic value of the blood pressure is at a certain phase relationship to the heart action. On the basis of this realization the operational safety of the pressure analyzer can be considerably increased. Thus the control system 60 contains one or more monostable multivibrators 98, 99 operated by the pulses of the amplitude discriminator 28. Always additional monostable multivibrators 9, 10 are connected in series in relation to the first mentioned monostable multivibrators. The last mentioned multivibrators thus form an electronic window for the pertinent characteristic value of the blood pressure. A characteristic value of the blood pressure is conducted on by way of an AND gate 100, 101 lying between the pressure analyzer 63 and the calculator 20 only whenever from a temporal point of view it occurs within the defined window.

The pump 55 is operated by way of two series of impulses. The non-critical pumping impulses are delivered by way of the line 54, the critical pumping impulses by way of the line 102. First of all these impulses are mixed in the OR gate 103. The pump is blocked in two different ways: 1 a positive signal at the outlet of the pressure cycle transmitter 21 leads by way of the logical combination 104 to a blocking of the pumping impulse at the logical AND gate 106, and 2. an occurrence at the outlet of the control system leads by way of the line 62 and a logical combination 105 lying in the line likewise to the blocking of the pumping function by way of the AND gate 106. The non-blocked pumping impulse is amplified in the output amplifier 107 and is conducted to the pumping element 108 which can be made preferably in the form of an electromagnetic valve.

The invention may be embodied in other specific forms without departing from the spirit or essential characteristics thereof. The embodiments are therefore to be considered in all respects as illustrative and not restrictive.

What is claimed is:

1. A method of controlling a heart pump for assisting the circulation of blood in an animal, comprising the steps of
    a. coupling a heart sensor system to the body of the animal,
    b. selecting by a pumping pulse computer a non-critical pumping pulse obtained by reference to the existing heart rate for starting circulation assistance,
    c. analyzing the blood pressure beat for beat to obtain a calculated heart beat frequency,
    d. continuously regulating the pump rate by reference to the calculated heart beat frequency thus obtained,
    e. automatically interrupting the pumping action for one or more cycles, and effecting comparison measurements between characteristic values of blood pressure with and without pulsation by a time and pulse controlled timer during said interruption of the natural heartbeat with the heartbeat immediately preceding said interruption, and
    f. stopping the pumping function of said mechanical heartpump in the event that the calculated heartbeat frequency is not obtained.

2. In a process for the automatic regulation of the mechanical support of heart circulation by way of the blood pressure, the steps of
    determining the heart frequency from an EKG of a patient,
    deriving an uncritical pumping impulse sequence, storing by way of several heart signals the characteristic values of the blood pressure, measured beat by beat, a heart pump being operated after switching on with the uncritical pulses supplied, interrupting by means of a time or pulse controlled measuring cycle transmitter said heart pump automatically for at least one and no more than several operating cycles in order to obtain (a) standard and (b) theoretical values of blood pressure produced by the heart without the aid of the pump, comparing stored preceding characteristic values of the blood pressure with the actual ones, and applying the comparative values to a regulator to cause a step by step enlargement of the operating cycle of the pump up to a rated value determined from the stored characteristic values of the blood pressure and comparing rhythm, frequency and amplitude of the actual characteristic values by way of a control system with the previously given standard values, the support of the circulation becoming effective precisely after the closure of the valves and the systolic pressure peak becomes minimal, whereby considerable deviations from the standard values cause the blocking first of all of the regulator and in case of a longer duration of the deviations also of that of the pump.

3. Apparatus for automatically controlling a heart synchronized circulating pump to control a patient's EKG and pressure parameters, said apparatus comprising, means coupling a heart sensor system to the body of a human patient whose heart is to be assisted by said pump and producing heart signals corresponding thereto, means for amplitude discriminating said heart signals, a period duration meter connected in series with said discriminator, a calculator connected to said meter for calculating an uncritical pumping pulse sequence, inlet means for the course of the blood pressure of the circulation, a pressure analyzer means connected in series with said inlet for determining the characteristic values of the blood pressure, means connecting the output of said analyzer over several heart cycles to said calculator, control line means for transferring the uncritical pumping impulses delivered by said calculator to a pump, a regulator connected to said pump, means connecting said calculator to said regulator for regulation of the operating cycles of said pump, a measuring cycle transmitter, circuit closer means for activating said measuring cycle transmitter, means connecting said amplitude discriminator with said measuring cycle transmitter, means connecting said measuring cycle transmitter both to said pump and said calculator, whereby for the control of the patient's EKG and pressure parameters a control system is provided and in that outlet lines both said regulator and said pump.

4. Apparatus as defined in claim 3 characterized in that said pressure analyzer includes a detector for identification of the phase and amplitude of the systolic and diastolic peak of the blood pressure, and a high pass filter — differentiator connected in series with said amplitude discriminator for identification of phase and amplitude of the valve closure.

5. Apparatus as defined in claim 3 wherein said pressure analyzer includes a frequency adjustable band-pass filter, a regulator controlled by said period duration meter for the adjustment of the selective frequency of the band-pass filter to precisely double the value of the heart frequency, and at least two detector series connected to said filter for identification of phase and amplitude of the systolic and diastolic peak of the blood pressure.

6. Apparatus as defined in claim 3 wherein said measuring cycle transmitter includes a monostable multivibrator, activated by a circuit closer having a scanning time of about 2 minutes, an astable multivibrator with approximately the same duration of the cycle, an electronic counter controlled by the EKG or the blood pressure, an AND gate for the connection of the output signals of said monostable multivibrator and of said counter an OR gate for the connection of the output of the astable multivibrator, and an AND gate for blocking of the pumping function and for reporting to said calculator.

7. Apparatus as defined in claim 3 wherein said calculator for processing of the amplitude and phase of the valve closure and/or of the systolic pressure peak has one or more electronic changeover switches controlled by the measuring cycle transmitter, a storage means for storing of amplitude and phase of the characteristic values of the blood pressure while said pump is in operation, additional storage means for storing of the values while said pump is switched off, a differential amplifier operated by signals from storage means, further amplitude discriminator means for limiting the signals from said storage means.

8. Apparatus as defined in claim 3 wherein said calculator for the determination of the tendency of amplitude and/or phase of the systolic and diastolic peak of the blood pressure always has an additional storage means for storing mean values, delay means controlled by the pulses of said amplitude discriminator, differential amplifier means operated by present and past values and an amplitude discriminator series connected with said differential amplifiers.

9. Apparatus as defined in claim 3 wherein said calculator for the calculation of an uncritical pumping impulse has a monostable multivibrator operated by the impulses of said amplitude discriminator, an additional monostable multivibrator connected in series, characteristic line amplifier means operated by said period duration meter for the frequency dependent influencing of the operating pulses of said monostable multivibrators and means supplying the said pump with control signals.

10. Apparatus as defined in claim 3 wherein said regulator has a monostable multivibrator operated by the pulses of said amplitude discriminator, an additional monostable multivibrator connected in series, regulator means operated by the control line therefor for the step by step control of the duration of the operating pulses, and electronic switch means lying in the said control line for blocking the regulating process.

11. Apparatus as defined in claim 3 wherein said control system has an amplitude discriminator, a logic circuit connected to the output of said amplitude discriminator for the detection of a low voltage in the EKG, a band filter means adapted to the supply frequency, a further amplitude discriminator connected to the output of said band filter means for the detection of external voltages in the EKG, a still further amplitude discriminator connected to said period duration meter for the detection of a tachycardia, a differential amplifier provided with variable RC section, a further amplitude discriminator connected to the output of said differential amplifier for the detection of arrhythmia of the period duration, and OR gate means connected to said discriminator and means supplying any output signal from said OR gate to said pump.

12. Apparatus as defined in claim 3 wherein said control system has at least one period duration meter operated by the characteristic values of the blood pressure, a differential amplifier provided with variable RC sections at the input thereof for the detection of arrhythmia of the period duration of the characteristic values of the blood pressure, a series connected amplitude discriminator, and a series connected OR gate, means connecting the output of said OR gate to said regulator.

13. Apparatus as defined in claim 3 wherein said control system in order to increase the operating safety of the data of said pressure analyzer has one or more monostable multivibrators operated by the pulses of the amplitude discriminator, and an additional monostable multivibrator and an AND gate lying between said pressure analyzer and said calculator.

14. Apparatus as defined in claim 3 wherein said pump has an OR gate operated by output signals from said calculator and said regulator, a logical circuit connected in the supply lines, an AND gate for blocking the pumping impulse transmitted by said OR gate, an output amplifier series connected with said AND gate and magnetic valve element controlled by said AND gate for initiating the pumping action of said pump.

* * * * *